United States Patent [19]

Barton et al.

[11] 4,434,080
[45] Feb. 28, 1984

[54] DEHYDROGENATION AGENTS BASED ON DERIVATIVES OF SELENIUM AND THEIR USE IN THE DEHYDROGENATION IN THE 1,4 POSITIONS OF STEROIDS

[75] Inventors: Derek H. R. Barton; William B. Motherwell, both of Gif-sur-Yvette, France

[73] Assignee: Roussel Uclaf, Paris, France

[21] Appl. No.: 379,434

[22] Filed: May 18, 1982

[30] Foreign Application Priority Data

May 19, 1981 [FR] France .............................. 81 09917

[51] Int. Cl.$^3$ ...................... B01J 31/04; B01J 31/02
[52] U.S. Cl. .................................. 502/152; 260/397.4
[58] Field of Search ................. 260/397.4; 252/426, 252/428, 434

[56] References Cited

U.S. PATENT DOCUMENTS 3,952,030  4/1976  Chambers et al. ......... 260/239.55 A
4,220,588  9/1980  Barton et al. .............. 260/239.55 A

OTHER PUBLICATIONS

Derek Barton et al., "Dehydrogenation of Steroidal and Triterpenoid Ketones etc., " J. Chem. Soc. Perkin I (1980) pp. 2209 to 2212.

Derek Barton et al., "Dehydrogenation of Steroidal Ketones, etc." J.C.S. Chem. Comm. (1978), pp. 130-131.

Meystre et al., "Gewinnung ven 1;4-Bisdehydro-3-oxo-steroiden", Helv. Chim. Acta 39, No. pp. 734-742 (1956).

*Primary Examiner*—Patrick Garvin
*Attorney, Agent, or Firm*—Hammond & Littell, Weissenberger and Muserlian

[57] ABSTRACT

Derivatives of selenium as dehydrogenation agents employed in the presence of an oxidation agent consisting of oxidized derivatives of possibly substiuted iodoaromatic compounds, particularly where the derivatives of selenium are employed in catalytic amounts; as well as a process of dehydrogenation 3-oxygenated steroids into the corresponding 3-oxygenated $\Delta^{1,4}$ steroids.

5 Claims, No Drawings

DEHYDROGENATION AGENTS BASED ON DERIVATIVES OF SELENIUM AND THEIR USE IN THE DEHYDROGENATION IN THE 1,4 POSITIONS OF STEROIDS

BACKGROUND OF THE DISCLOSURE

The present invention concerns new dehydrogenation agents based on derivatives of selenium and their use in the dehydrogenation in the 1,4 positions of steroids.

Derivatives of selenium are known as dehydrogenation agents. In particular, it is possible to dehydrogenate in the 1,4 position those steroids having a ketone function in the 3 position, as described by DHR Barton et al in J. Chem. Soc. Perkin I (1980), pages 2209 to 2212. In this procedure, benzene-seleninic anhydride is employed. However, this method presents two important inconveniences:

(a) This is a costly method, due to the high price of benzene-seleninic anhydride;

(b) This is a method which gives rise to secondary reactions due to the formation of selenic acid or other derivatives occurring from the reduction of the benzene-seleninic anhydride. These two inconveniences make the method difficult to utilize on an industrial scale.

While the authors disclose one example to a catalytic dehydrogenation of Lanostan-3-one using t.-butylhydroperoxide and diphenyl diselenide, the yield of the desired lanost-1-en-3-one was relatively low and the product obtained had a low melting point range, indicating contamination.

Other methods of dehydrogenation of 3-keto steroids employing aryl-seleninic anhydride are described in U.S. Pat. No. 4,220,588 to Barton et al, and Barton et al, J.C.S. Chem. Comm. (1978), pages 130-1. In addition, Meystre et al Helv. Chim. Acta 39, No. 3 pages 734-742 (1956) describes dehydrogenating $\Delta^4$-3-oxo-steroids employing selenium dioxide as a dehydrogenation agent.

OBJECTS OF THE INVENTION

An object of the present invention is the development of a dehydrogenation agent based on derivatives of selenium which avoids the drawbacks of the prior art and gives $\Delta^{1,4}$-3-oxo-steroids in excellent yields.

Another object of the present invention is the development of a derivative of selenium as a dehydrogenation agent employed in the presence of an oxidation agent consisting of an oxidized derivative of a possibly substituted iodoaromatic compound.

A further object of the invention is the development of a process for dehydrogenation 3-oxygenated steroids into the corresponding $\Delta^{1,4}$-3-oxygenated steroids employing the above dehydrogenation agent.

These and other objects of the invention will become more apparent as the description thereof proceeds.

DESCRIPTION OF THE INVENTION

It has now been discovered that it is possible to use the derivatives of selenium industrially as dehydrogenation agents without the drawbacks above recited.

In particular the invention relates to a derivative of selenium selected from the group consisting of the organic derivatives of selenium, selenic acid and selenium oxide as dehydrogenation agent employed in the presence of an oxidation agent consisting of an oxidized derivative of a possibly substituted iodoaromatic compound. By employing the aforesaid dehydrogenation agent, the derivatives of selenium can be employed in a catalytic amount in the presence of the oxidation agent.

The invention therefore resides in that the aforesaid oxidation agent is utilized in order to oxidize the reduced form of the derivative of selenium utilized. It is then possible to utilize catalytic amounts of the derivative of selenium, which makes the process economically affordable.

The derivatives of selenium which are preferable are diphenyl diselenide, benzene-seleninic anhydride benzene-seleninic acid, selenic acid and selenium oxide. More particularly diphenyl diselenide or benzene seleninic anhydride is employed.

The derivative of selenium, after being reduced during the dehydrogenation is oxidized anew. Thus there is no formation of secondary reactions due to the formation of selenic acid or other derivatives arising from the reduction of the derivatives of selenium utilized.

The reaction can thus be shown as follows:

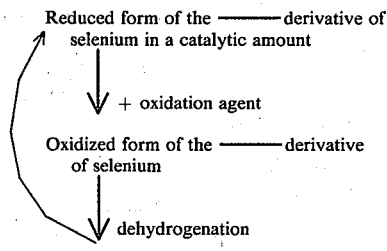

The invention more particularly relates to a dehydrogenation agent consisting of a catalytic amount of diphenyldiselenide in the presence of an oxidation agent consisting of an oxidized derivative of a possibly substituted iodoaromatic compound.

The mechanism of the action is as follows:

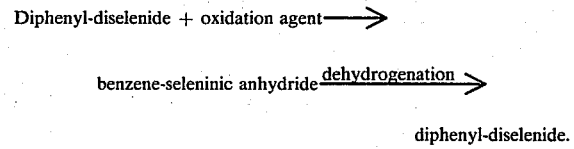

The invention thus consists in the "in situ" formation of benzene-seleninic anhydride.

It is very intertesting from the economic point of view to utilize diphenyl-diselenide, however other derivatives of selenium, particularly oxygenated derivatives can be utilized, especially benzene-seleninic anhydride itself.

A further object of the invention therefore is a dehydrogenation agent consisting of a catalytic amount of benzene-seleninic anhydride in the presence of an oxidation agent consisting of an oxidized derivative of a possibly substituted iodoaromatic compound.

The invention particularly relates to a dehydrogenation agent consisting of the above recited derivatives of selenium when they are use in a catalytic amount in the presence of a compound selected from the group consisting of iodoxy-benzene, meta-iodoxybenzoic acid and compounds having the formula

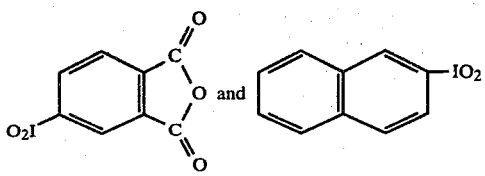

Most especially the invention relates to a dehydrogenation agent consisting of diphenyl-diselenide used in a catalytic amount in the presence of meta-iodoxybenzoic acid.

It is of particular interest to employ meta-iodoxybenzoic acid as the oxidation agent, since it is possible to readily recover the meta-iodoxybenzoic acid and the diphenyl-diselenide which were not utilized in the reaction, without chromatography, as it is indicated later in the examples.

The dehydrogenation agents of the invention are principally adapted to the dehydrogenation in the 1 and 4 positions of steroids or of related chemical products.

The invention also therefore has as an object a process for dehydrogenation employing a derivative of selenium as a dehydrogenation agent employed in the presence of an oxidation agent consisting of an oxidized derivative of a possibly substituted iodoaromatic compound, consisting essentially of (1) subjecting a compound having the formula I

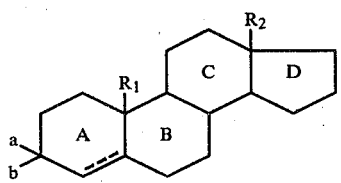

wherein $R_1$ is selected from the group consisting of hydrogen, alkyl having from 1 to 4 carbon atoms, haloalkyl having from 1 to 4 carbon atoms, cyano, aminoalkyl having from 1 to 4 carbon atoms, hydroxyalkyl having from 1 to 4 carbon atoms, alkoxyalkyl having from 2 to 4 carbon atoms, alkanal having from 1 to 4 carbon atoms, alkanoyl having from 2 to 4 carbon atoms, alkenyl having from 2 to 4 carbon atoms and alkynyl having from 2 to 4 carbon atoms; $R_2$ is alkyl having from 1 to 4 carbon atoms;

is a member selected from the group consisting of

and keto; the dashed line represents a possible double bond in the 4(5) position; the B, C and D rings optionally contain one or several double bonds; and the A,B, C and D rings are optionally substituted by a member selected from the group consisting of:

(a) at least one hydroxyl or ketone,
(b) at least one halogen
(c) at least one linear or branched alkyl having from 1 to 10 carbon atoms optionally substituted by at least one function selected from the group consisting of ketone, hydrocarbon acyloxy having from 1 to 18 carbons and alkoxycarbonyl having from 2 to 5 carton atoms, (d) at least one linear or branched alkoxy having from 1 to 4 carbon atoms,
(e) at least one hydrocarbon acyloxy having from 1 to 18 carbon atoms, and
(f) at least one alkenyl or alkynyl having from 2 to 4 carbon atoms;

to the action of the above dehydrogenation agent and (2) obtaining the corresponding $\Delta^{1,4}$ compound having the formula II

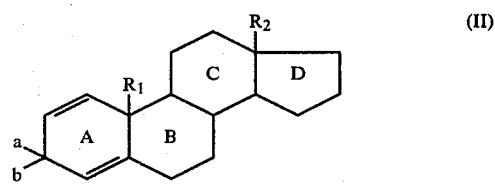

wherein $R_1$, $R_2$, a,b and the possible substituents have the above-assigned meanings.

Where $R_1$ represents an alkyl, it preferably is methyl or ethyl. Where $R_1$ represents an oxygenated alkyl, it preferably is hydroxymethyl, hydroxyethyl, formyl or acetyl. Where $R_1$ represents an azotic alkyl, it preferably is cyano, aminomethyl or aminoethyl. Where $R_1$ represents a haloalkyl, it preferably is halomethyl, $-CH_2Hal$, where Hal represents a halogen, such as, for example, chlorine, fluorine or bromine. Where $R_1$ represents an alkenyl, it preferably is vinyl or allyl. Where $R_1$ represents alkynyl, it preferably is ethynyl.

$R_2$ preferably represents methyl or ethyl.

Where the B, C and D rings contain one or several double bonds, these are preferably double bonds in the 9(11) and/or the 16(17) positions or a system of conjugated double bonds in the 3(4) and 5(6) positions or in the 4(5) and 6(7) positions.

Where the A, B, C and D rings are substituted by a hydroxyl, it is preferably a 3-hydroxyl or 11-hydroxyl. Where the A, B, C and D rings are substituted by Ketone function it is preferably a Ketone function in the 3 or 11 position. Where the A, B, C and D rings are substituted by a halogen, it is preferably fluorine, chlorine or bromine in the 6 or $9\alpha$ position, for example. Where the A, B, C and D rings are substituted by one or several alkyls, these are preferably methyl or ethyl in the 2, 6, 7, $16\alpha$ or $16\beta$ positions or an alkyl in the 17 position. Where the A, B, C and D rings are substituted by an alkoxy, these are preferably a methoxy or an ethoxy in the 3 or $11\beta$ position. Where the A, B, C and D rings are substituted by alkenyl, it is preferably vinyl or allyl in the $11\beta$ position, for example. Where the A, B, C and D rings are substituted by alkynyl, it is preferably ethynyl in the $11\beta$ position. The hydrocarbon acyloxy groups are preferably acetyloxy or propionyloxy. The alkoxycarbonyl groups are preferably methoxycarbonyl or ethoxycarbonyl.

The invention particularly has as an object, the use of the dehydrogenation agents of the invention where the starting compound of formula I has $R_1$ and $R_2$ representing methyl and

representing a keto group. Moreover, it is preferable to utilize starting compounds of formula I wherein the D ring is substituted, most preferably in the 17 position. The invention naturally most particularly relates to the use of the dehydrogenation agents of the invention as described in the examples.

The invention equally has as its object the use of the dehydrogenation agents of the invention in order to prepare the products II below starting from the corresponding products I.

ally in the synthesis of therapeutically active products: see, for example, Belgian Pat. Nos. 545,877 or 682,889.

The following examples are illustrative of the invention without being limitative in any respect.

EXAMPLE 1

17α-acetoxy-16β-methyl-pregna-1,4,9(11)-triene-3,20-dione 720 mg of m-iodoxybenzoic acid and 52 mg of diphenyl-diselenide in 20 cc of toluene were heated to reflux

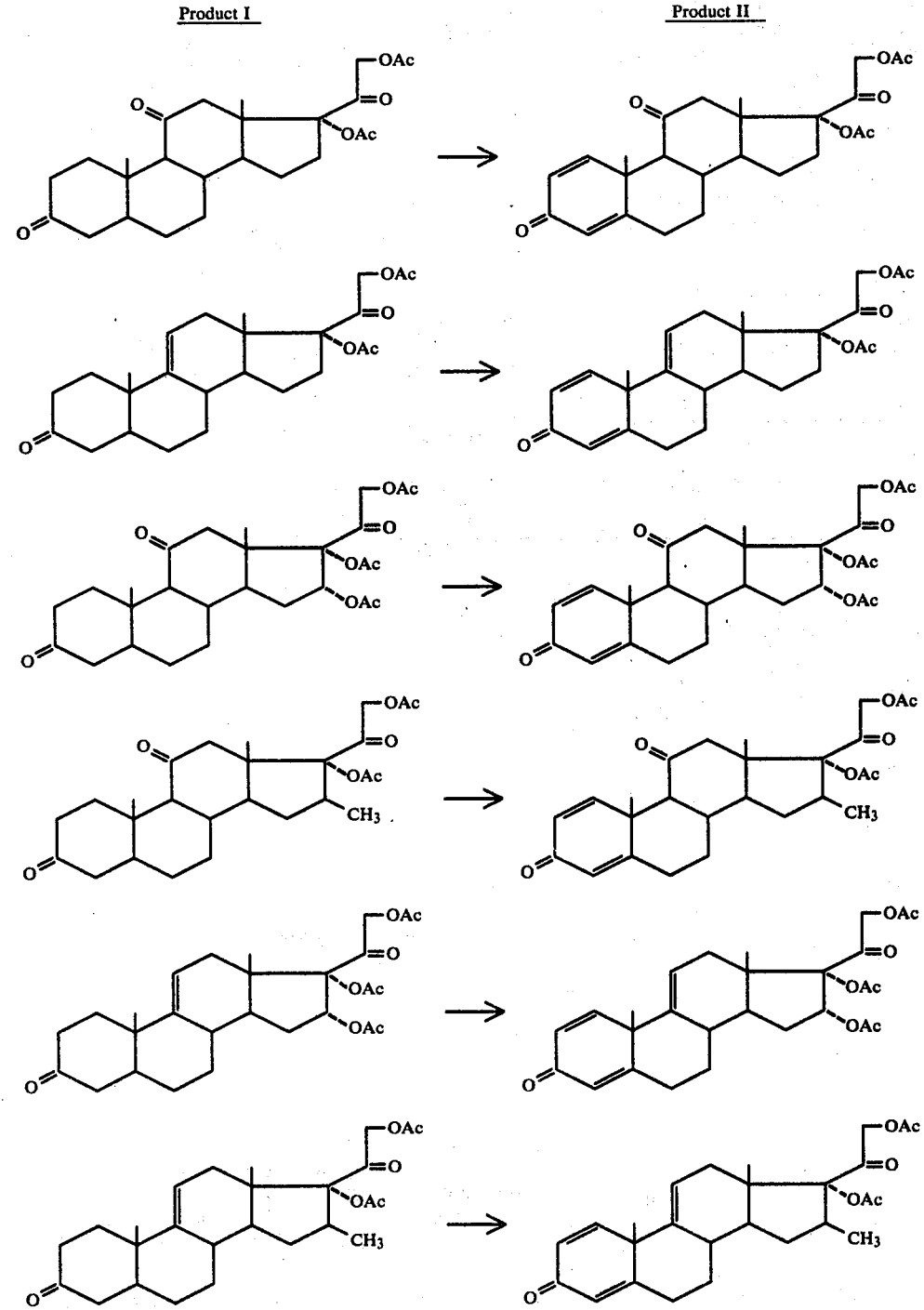

The products resulting from the dehydrogenation are chemical products known in therapy or used industrifor a period of 15 minutes. Then, 300 mg of 17α-acetoxy-16β-methyl-5β-H-pregna-9(11)-ene-3,20-dione were added thereto and the mixture was heated again to reflux for a period of 2½ hours. The mixture was then cooled and extracted with a saturated solution of sodium bicarbonate, washed with water and evaporated to dryness. The product obtained was recrystallized from a mixture of acetone and hexane. 255 mg of the desired product were obtained melting at 230° to 233° C. and having a specific rotation $\alpha_D^{19} = +10°$ (c=0.9% $CHCl_3$).

The aqueous phases were combined and reduced by treatment at room temperature with a saturated solution of sodium hydrosulfite for one hour. After extraction with toluene and evaporating to dryness, 47 mg (being 90%) of the diphenyl-diselenide were thus recovered. After oxidizing the aqueous phase by passing a stream of air through for one hour in order to destroy the excess of the hydrosulfite, the solution was acidified with dilute sulfonic acid. By filtration, washing and drying, 550 mg of meta-iodo-benzoic acid were obtained.

EXAMPLES 2 TO 14

The following Table gives the details of the preparation of the products II according to the process of Example 1 above.

The preceding specific embodiments are illustrative of the practice of the invention. It is to be understood, however, that other expedients known to those skilled in the art or disclosed herein may be employed without departing from the spirit of the invention or the scope of the appended claims.

We claim:

1. A derivative of selenium selected from the group consisting of diphenyl diselenide, benzene seleninic anhydride, benzene seleninic acid, selenic acid and selenium oxide employed in the presence of an oxidation agent consisting of an oxidized derivative of a possibly substituted iodoaromatic compound selected from the group consisting of iodoxy-benzene, metaiodoxy-benzoic acid,

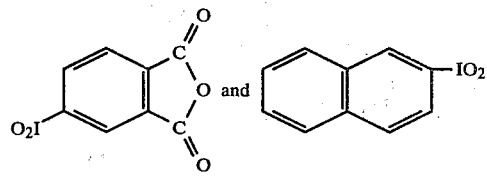

as a dehydrogenation agent.

2. The dehydrogenation agent of claim 1 wherein said derivative of selenium is employed in a catalytic

TABLE

| | | Conditions of the Reaction | | | Corresponding Products II Obtained | |
|---|---|---|---|---|---|---|
| | | | | | Equivalent Amounts | |
| Example | Starting Products I | Time (hours) | Solvent/ T °C. | Catalyst Equivalent | Expressed as Iodoxybenzene | Yield |
| 2 | Cholestan-3-one | 24 | $S_1$ | $C_1$ (0.2) | $M_1$ (3.3) | 84% |
| 3 | Cholestan-3β-ol | 24 | $S_1$ | $C_1$ (0.2) | $M_1$ (3.3) | 81% |
| 4 | Cholestan-3β-ol | 12 | $S_1$ | $C_1$ (0.2) + TsOH (trace) | $M_1$ (3.3 | 77% |
| 5 | Androst-4-en-3,17-dione | 12 | $S_1$ | $C_1$ (0.16) | $M_1$ (3.6) | 72% |
| 6 | Pregna-4-en-3,11,20-trione | 12 | $S_1$ | $C_1$ (0.18) | $M_1$ (3.3) | 51% |
| 7 | Cholestan-3β-ol | 20 | $S_1$ | $C_1$ (0.2) | $M_2$ (3.3) | 74% |
| 8 | Cholestan-3β-ol | 3 | $S_2$ | $C_2$ (0.2) | $M_2$ (3.3) | 88% |
| 9 | Cholestan-3β-ol | 2 | $S_3$ | $C_2$ (0.2) | $M_2$ (3.3) | 79% |
| 10 | Cholestan-3β-ol | 16 | $S_2$ | $C_2$ (0.3) | $M_2$ (4.16) | 73% |
| 11 | Methyl 3α-hydroxy-5β-cholanoate | 3 | $S_2$ | $C_2$ (0.2) | $M_2$ (3.3) | 84% |
| 12 | 17α-acetoxy-16β-methyl-5β-pregna-9(11)-en-3,20-dione | 2.5 | $S_2$ | $C_2$ (0.2) | $M_2$ (3.2) | 86% |
| 13 | 17α-acetoxy-16β-methyl-5β-pregna-9(11)-en-3,20-dione | 2.5 | $S_2$ | $C_1$ (0.14) | $M_2$ (3.0) | 75% |
| 14 | Cholestan-3-one | 3 | $S_3$ | $C_3$ (0.5) | $M_1$ (3.0) | 58%) |

Reactants and Solvents:
$S_1$ = benzene at reflux,
$S_2$ = toluene at reflux,
$S_3$ = chlorobenzene at reflux,
$C_1$ = benzene-seleninic anhydride,
$C_2$ = diphenyl-diselenide,
$C_3$ = selenium dioxide,
$M_1$ = iodoxybenzene,
$M_2$ = meta-iodoxybenzoic acid,
TsOH = toluenesulfonic acid.

In the Table the numbers for the equivalents are the amounts charged where 1 is the theoretical amount required for the dehydrogenation. These results show that as little as 0.03 equivalents of diphenyl-diselenide are sufficient to dehydrogenate a steroid, such as cholestan-3β-ol with a 73% yield of the desired cholesta-1,4-dien-3-one.

amount.

3. The dehydrogenation agent of claim 2 wherein said derivative of selenium is diphenyl-diselenide.

4. The dehydrogenation agent of claim 2 wherein said derivative of selenium is benzene-seleninic anhydride.

5. A dehydrogenation agent consisting of a catalytic amount of diphenyl-diselenide in the presence of a meta-iodoxybenzoic acid.

* * * * *